(12) United States Patent
Bechtel

(10) Patent No.: US 10,674,136 B2
(45) Date of Patent: Jun. 2, 2020

(54) DEVICE FOR CAPTURING A STEREOSCOPIC IMAGE

(71) Applicant: Karl Storz SE & Co. KG, Tuttlingen (DE)

(72) Inventor: Christin Bechtel, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 15/699,443

(22) Filed: Sep. 8, 2017

(65) Prior Publication Data

US 2018/0077404 A1    Mar. 15, 2018

(30) Foreign Application Priority Data

Sep. 9, 2016    (DE) .......................... 10 2016 117 024

(51) Int. Cl.
*H04N 13/246*    (2018.01)
*H04N 13/296*    (2018.01)
(Continued)

(52) U.S. Cl.
CPC ....... *H04N 13/246* (2018.05); *A61B 1/00193* (2013.01); *G02B 7/09* (2013.01);
(Continued)

(58) Field of Classification Search
None
See application file for complete search history.

(56) References Cited

U.S. PATENT DOCUMENTS

| 4,879,596 A | 11/1989 | Miura et al. |
| 7,768,702 B2 * | 8/2010 | Hirose ............... A61B 1/00193 359/378 |

(Continued)

FOREIGN PATENT DOCUMENTS

| DE | 10255460 A1 | 6/2004 |
| EP | 2472318 A1 | 7/2012 |

(Continued)

OTHER PUBLICATIONS

Extended European Search Report Application No. 17190167.1 Completed Date: Jan. 18, 2018; dated Jan. 26, 2018 8 pages.
(Continued)

*Primary Examiner* — Chikaodili E Anyikire
(74) *Attorney, Agent, or Firm* — Whitmyer IP Group LLC

(57) ABSTRACT

A device for capturing a stereoscopic image includes a first image sensor including a first light-sensitive layer for capturing a first image, a second image sensor including a second light-sensitive layer for capturing a second image, a first lens including a first image-side principal plane, which first lens images points lying in a first area sharply onto the first light-sensitive layer of the first image sensor, and a second lens including a second image-side principal plane, which second lens images points lying in a second area sharply onto the second light-sensitive layer of the second image sensor. The distance between the first image-side principal plane of the first lens and the first light-sensitive layer of the first image sensor and the distance between the second image-side principal plane of the second lens and the second light-sensitive layer of the second image sensor are different.

17 Claims, 8 Drawing Sheets

(51) Int. Cl.
*H04N 13/239* (2018.01)
*A61B 1/00* (2006.01)
*G02B 21/22* (2006.01)
*G03B 35/10* (2006.01)
*G02B 7/09* (2006.01)
*H04N 5/225* (2006.01)

(52) U.S. Cl.
CPC ............ *G02B 21/22* (2013.01); *G03B 35/10* (2013.01); *H04N 5/2254* (2013.01); *H04N 13/239* (2018.05); *H04N 13/296* (2018.05); *H04N 2213/001* (2013.01)

(56) References Cited

U.S. PATENT DOCUMENTS

| | | | |
|---|---|---|---|
| 2003/0072483 A1 | 4/2003 | Chen | |
| 2011/0018972 A1* | 1/2011 | Pan | H04N 5/23212 348/47 |
| 2012/0140044 A1* | 6/2012 | Galstian | A61B 1/00193 348/47 |
| 2012/0154547 A1* | 6/2012 | Aizawa | G02B 7/285 348/47 |
| 2013/0038689 A1* | 2/2013 | McDowall | G02B 27/0075 348/45 |
| 2015/0156478 A1 | 6/2015 | Ono | |
| 2017/0358062 A1* | 12/2017 | Podnar | G06T 5/006 |

FOREIGN PATENT DOCUMENTS

| | | |
|---|---|---|
| EP | 2493203 A2 | 8/2012 |
| EP | 2597502 A1 | 5/2013 |
| WO | 9410604 A1 | 5/1994 |

OTHER PUBLICATIONS

DE Search Report Application No. DE 10 2016117 024.0 Completed Date: Sep. 9, 2016; dated Mar. 28, 2017 6 pages.

* cited by examiner

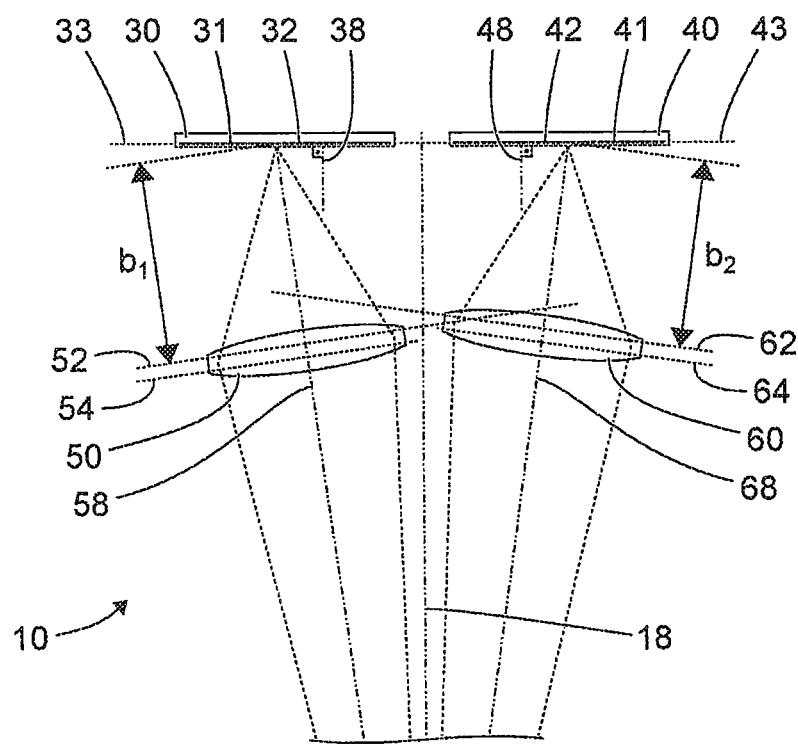
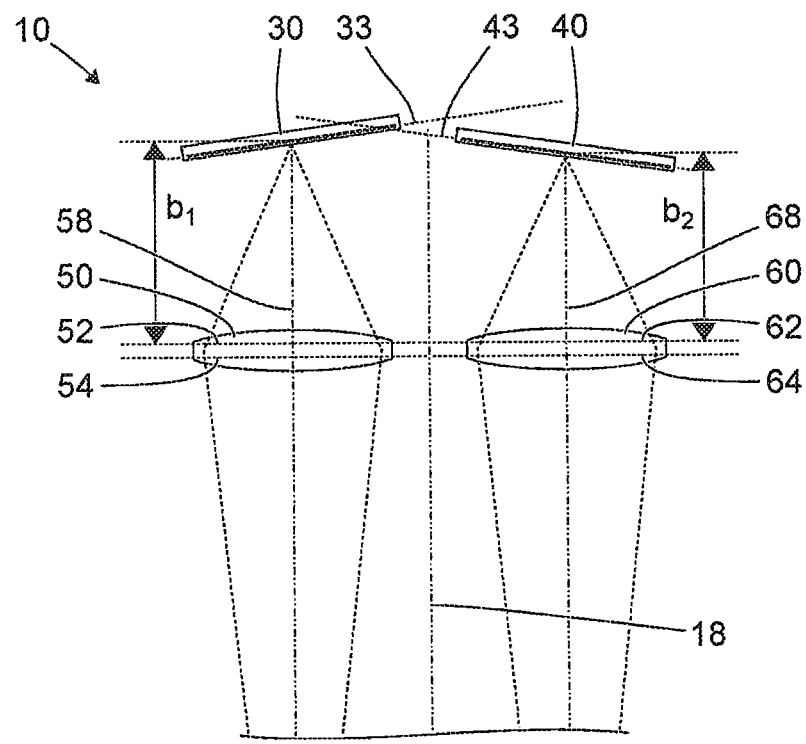

DEVICE FOR CAPTURING A STEREOSCOPIC IMAGE

TECHNICAL FIELD

The present invention is related to a stereo exoscope, a stereo surgical microscope, a stereo endoscope and other devices for capturing a stereoscopic image, and to a method for adjusting a device for capturing a stereoscopic image.

BACKGROUND

In the representation of stereoscopic images, the depth of field has a significant influence on the quality of the spatial impression that arises for the observer. A minimum depth of field is required in order to bring about a spatial or three-dimensional impression. On the other hand, a very large depth of field may cause a simultaneous sharp representation of objects at very different distances and therefore with very different disparities and may therefore be perceived as unpleasant.

Attempts are made in many cases to generate a high-resolution image with a large aperture stop. The larger the aperture stop, the smaller the depth of field.

US 2012/0140044 A1 describes capture of a stereoscopic image by means of two liquid crystal lens elements, the focal lengths of which can be set independently of one another (paragraphs [0057], [0083]). The two liquid crystal lens elements are set such that a viewed object lies near the distal limit of the depth of field range of the image captured for the left eye and near the proximal limit of the depth of field range of the image captured for the right eye (FIG. 14C).

US 2011/0018972 A1 describes a stereoscopic imaging device comprising two lenses, wherein a different focusing of both lenses is intended to be avoided (paragraphs [0011], [0013], [0014]).

US 2015/0156478 A1 mentions a 3D representation (paragraph).

SUMMARY

It is an object of the present invention to provide an improved device for capturing a stereoscopic image and an improved method for adjusting a device for capturing a stereoscopic image.

This object is achieved by use of the subjects of the independent claims.

Developments are specified in the dependent claims.

A device for capturing a stereoscopic image comprises a first image sensor comprising a first light-sensitive layer for capturing a first image, a second image sensor comprising a second light-sensitive layer for capturing a second image, a first lens, which images points lying in a first area sharply onto the first light-sensitive layer of the first image sensor, and a second lens, which images points lying in a second area sharply onto the second light-sensitive layer of the second image sensor, wherein in the center of a region which is imaged both onto the first image sensor by the first lens and onto the second image sensor by the second lens, the first area and the second area are spaced apart from one another.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein at least one of a first straight line through the center of the first light-sensitive layer of the first image sensor and through the center of the second light-sensitive layer of the second image sensor and a second straight line through the center of the first image-side principal plane of the first lens and through the center of the second image-side principal plane of the second lens is not orthogonal to a principal viewing axis of the device.

The center of a light-sensitive layer of an image sensor is, in particular, the area centroid of that region of the light-sensitive layer from which image data are actually read out and processed further during the envisaged use of the device. The center of a principal plane of a lens is the point of intersection of the principal plane with the optical axis of the lens.

This arrangement has the effect, in particular, that the first area and the second area are spaced apart or offset in a direction parallel to the principal viewing axis of the device.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein the first image sensor and the first lens are not arranged mirror-symmetrically with respect to the second image sensor and the second lens.

In particular, the first image sensor and the first lens are not mirror-symmetrical with respect to the second image sensor and the second lens.

The asymmetrical arrangement has the effect, in particular, that the first area and the second area are spaced apart or offset in a direction parallel to the principal viewing axis of the device.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein no plane of symmetry exists with respect to which the first image sensor and the second image sensor and also the first lens and the second lens are arranged mirror-symmetrically.

In particular, the arrangement of the first image sensor and of the first lens is not mirror-symmetrical with respect to the arrangement of the second image sensor and of the second lens.

The asymmetrical arrangement has the effect, in particular, that the first area and the second area are spaced apart or offset in a direction parallel to the principal viewing axis of the device.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein at least either the first light-sensitive layer of the first image sensor and the second light-sensitive layer of the second image sensor are arranged in two planes which are parallel and spaced apart from one another, or the first image-side principal plane of the first lens and the second image-side principal plane of the second lens are parallel and spaced apart from one another.

This arrangement has the effect, in particular, that the first area and the second area are spaced apart or offset in a direction parallel to the principal viewing axis of the device.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein the distance between the first image-side principal plane of the first lens and the first light-sensitive layer of the first image sensor and the distance between the second image-side principal plane of the second lens and the second light-sensitive layer of the second image sensor are different, such that the first area and the second area are spaced apart or offset in a direction parallel to the principal viewing axis of the device.

The device is, in particular, a stereo surgical microscope, some other stereo microscope, a stereo exoscope or a stereo endoscope for applications in medicine and/or for technical or other non-medical applications. Alternatively, the device may be part of a stereo surgical microscope, of some other stereo microscope, of a stereo exoscope or of a stereo endoscope for applications in medicine and/or for technical or other non-medical applications.

The first image sensor and the first lens jointly form in particular a first monocular camera. The second image sensor and the second lens together form in particular a second monocular camera. Between the two monocular cameras there need not but may be a partial or complete spatial and/or constructional separation. Each of the two monocular cameras may comprise a plurality of image sensors for converting light in different wavelength ranges into electrical or other signals.

The first image sensor and the second image sensor may be embodied as two separate components (for example CCD or CMOS or other semiconductor components), which optionally are also spaced apart from one another spatially. Alternatively, the first image sensor may be formed by a first region of a component and the second image sensor may be formed by a second region of the same component, wherein the first region and the second region of the component are spaced apart from one another, in particular.

The first image sensor is configured in particular for capturing a first image provided—optionally after amplification, processing and conditioning—for viewing by the left eye of an observer. The second image sensor is configured in particular for capturing a second image provided for simultaneous viewing by the right eye of the observer. Alternatively, the first image may be provided for viewing by the right eye, and the second image for viewing by the left eye.

The images captured by means of the image sensors may be reproduced simultaneously or alternately by one and the same screen with different colors or different polarizations or alternately in different time intervals. In particular, spectacles to be worn by the observer ensure here that the observer's left eye can see only the first image and the observer's right eye can see only the second image (or vice versa). Alternatively, an assigned screen may be provided for example for each eye of an observer.

The first lens and the second lens may each comprise one or more lens elements or other optical elements, wherein each optical element comprises one or more curved light-refracting or light-reflecting areas and/or has a refractive index that varies in a location-dependent manner (for example GRIN lens elements), or diffracts light. The first lens and the second lens comprise in particular aperture stops having an identical diameter and/or identical area. The first lens and the second lens are structurally identical, in particular.

The light-sensitive layers of the image sensors are in particular so thin that they may be regarded as two-dimensional objects, namely areas, in particular planar areas, in the present technical context. Each lens images—apart from diffraction effects and other imaging aberrations—each first point in the object space onto a second point in the image space. Thus, for each punctiform or areal object on the object side there is a corresponding punctiform or areal image on the image side of the lens. The imaging behavior of many lenses is described at least approximately by the lens element equation $1/g+1/b=1/f$, wherein g is the object distance (the distance between an object and an object-side principal plane of the lens), b is the image distance (the distance between the image of the object and an image-side principal plane of the lens) and f is the focal length of the lens. The focal length f and the positions of the object-side and image-side principal planes are characteristic variables of every lens.

The first area is the—ideally planar—object area which corresponds to the first light-sensitive layer of the first image sensor, that is to say which is imaged sharply into the first light-sensitive layer of the first image sensor by the first lens. From a punctiform object which does not lie in the first area, the first lens generates a non-punctiform image in the first light-sensitive layer of the first image sensor. The non-punctiform image is also referred to as circle of least confusion or circle of confusion. The size of the non-punctiform image is dependent on the distance between the punctiform object and the first area.

The second area is the—ideally planar—object area which corresponds to the second light-sensitive layer of the second image sensor, that is to say which is imaged sharply into the second light-sensitive layer of the second image sensor by the second lens. From a punctiform object which does not lie in the second area, the second lens generates a non-punctiform image in the second light-sensitive layer of the second image sensor. The size of the non-punctiform image is dependent on the distance between the punctiform object and the second area.

If the first area which is imaged sharply into the first light-sensitive layer of the first image sensor and the second area which is imaged sharply into the second light-sensitive layer of the second image sensor are in each case planar, parallel to one another and spaced apart from one another, they do not intersect one another. If the first area and the second area are in each case non-planar, they intersect one another in general even if they are arranged offset relative to one another. However, the line of intersection then in general does not lie on the principal viewing axis of the device.

The center of the region which is imaged both onto the first image sensor by the first lens and onto the second image sensor by the second lens lies in particular on a straight line that defines the principal viewing axis of the device.

In the case of parallel optical axes of the lenses, the principal viewing direction is the direction of the optical axes and the principal viewing axis is the straight line which is parallel to the optical axes of the lenses and which lies in that plane which contains both optical axes, and which is at identical distances from both optical axes. In this case, the center of the region which is imaged both onto the first image sensor by the first lens and onto the second image sensor by the second lens is, in particular, the center between the optical axes of the lenses.

In the case of intersecting optical axes, the principal viewing axis of the device is, in particular, the direction of that angle bisecting straight line in the plane defined in the optical axes of the lenses which forms identical angles with both optical axes, and which lies between the lenses.

In the case of skew (i.e. neither parallel nor intersecting) optical axes of the lenses, the principal viewing axis is that straight line which forms minimal angles with both optical axes, and which is arranged such that for each plane orthogonal to the straight line the point of intersection of the straight line with said plane lies in the center between the points of intersection of the optical axes with said plane.

If the image-side principal plane of the first lens is not parallel to the first light-sensitive layer of the first image sensor, the distance between the image-side principal plane of the first lens and the first light-sensitive layer of the first image sensor is the distance between the point of intersection of the optical axis of the first lens with the image-side principal plane of the first lens and the point of intersection of the optical axis of the first lens with the first light-sensitive layer of the first image sensor.

If the image-side principal plane of the second lens is not parallel to the second light-sensitive layer of the second image sensor, the distance between the image-side principal plane of the second lens and the second light-sensitive layer of the second image sensor is the distance between the point of intersection of the optical axis of the second lens with the second image-side principal plane of the second lens and the point of intersection of the optical axis of the second lens with the second light-sensitive layer of the second image sensor.

The first lens and the second lens may facilitate imaging of very high quality or having only comparatively small imaging aberrations. Focusing onto different areas by means of different distances between the image-side principal planes and the light-sensitive layers of the image sensors constitutes a purely mechanical task which can be achieved permanently and in particular mechanically robustly. Taking account of—in particular thermally—sensitive liquid crystal lens elements is not necessary; the complex electronic driving of liquid crystal lens elements is obviated.

In the case of a device such as is described here, the first lens and the second lens have in particular the same focal length.

The first lens and the second lens have the same focal length in particular nominally or within the manufacturing tolerances. An offset or a distance between the first area, in which there are points which are imaged sharply onto the first light-sensitive layer of the first image sensor by the first lens, and the second area, in which there are points which are imaged sharply onto the second light-sensitive layer of the second image sensor by the second lens, is able to be realized solely by means of different image distances or distances between the image-side principal planes and the assigned light-sensitive layers.

In the case of a device such as is described here, in particular the first image-side principal plane of the first lens and the second image-side principal plane of the second lens are parallel and spaced apart from one another.

In the case of a device such as is described here, the light-sensitive layers of the image sensors lie in particular in the same plane.

In the case of a device such as is described here, the light-sensitive layers of the image sensors lie in particular in the same plane, wherein the first image-side principal plane of the first lens and the second image-side principal plane of the second lens are parallel to one another and spaced apart from one another or the line of intersection of the image-side principal planes of the lenses does not intersect the principal viewing axis of the device.

Two planes that are not parallel intersect in a straight line of intersection. If the line of intersection of the principal planes of the lenses does not intersect the principal viewing axis of the device, it is situated laterally with respect to the principal viewing direction. This is tantamount to the principal planes not being arranged mirror-symmetrically.

A parallel arrangement of the principal planes of the lenses is taken to mean a parallel arrangement of the principal planes within the manufacturing tolerances. An arrangement of the principal planes of the lenses spaced apart from one another is taken to mean a distance between the principal planes of the lenses which is greater than the manufacturing tolerance of the positions of the principal planes of the lenses.

An arrangement of the image-side principal planes of the lenses parallel and spaced apart from one another corresponds mathematically to an arrangement of the line of intersection of the principal planes at infinity. The line of intersection of the image-side principal planes of the lenses does not intersect the principal viewing axis of the device if the distance thereof from the principal viewing axis lies outside the manufacturing tolerances.

A distance between the line of intersection of the image-side principal planes of the lenses and the principal viewing axis characterizes—even in the case of non-parallel optical axes of the lenses—an asymmetrical arrangement of the image-side principal planes of the lenses of the device. Said asymmetrical arrangement of the image-side principal planes of the lenses facilitates a divergence of the first area, in which there are points that are imaged sharply onto the first light-sensitive layer of the first image sensor, and the second area, in which there are points that are imaged sharply onto the second light-sensitive layer of the second image sensor.

In the case of a device such as is described here, in particular the first light-sensitive layer of the first image sensor lies in a first plane and the second light-sensitive layer of the second image sensor lies in a second plane, wherein the first plane and the second plane are parallel and spaced apart from one another.

In the case of a device such as is described here, the light-sensitive layers of the image sensors lie in particular in two different planes which are parallel and spaced apart from one another or the line of intersection of which does not intersect the principal viewing axis of the device.

An arrangement of the light-sensitive layers of the image sensors in two different planes can be combined with an arrangement of the image-side principal planes of the lenses in one plane or in two mutually different planes in order to cause a divergence of the first area, which is imaged sharply onto the first light-sensitive layer of the first image sensor, and the second area, which is imaged sharply onto the second light-sensitive layer of the second image sensor.

In the case of a device such as is described here, the first image-side principal plane of the first lens and the second image-side principal plane of the second lens are identical, in particular, wherein the image sensors are arranged such that the light-sensitive layers of the image sensors lie in two planes which are parallel and spaced apart from one another.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein the first lens and the second lens are identical to one another, wherein the distance between the first lens and the first image sensor is identical to the distance between the second lens and the second image sensor, and wherein the first lens and the second lens are arranged offset in the direction of the principal viewing axis of the device, such that the first area and the second area are spaced apart or offset in a direction parallel to the principal viewing axis of the device.

A device for capturing a stereoscopic image comprises a first image sensor comprising a first light-sensitive layer for capturing a first image, a second image sensor comprising a second light-sensitive layer for capturing a second image, a first lens comprising a first image-side principal plane, which first lens images points lying in a first area sharply onto the first light-sensitive layer of the first image sensor, and a second lens comprising a second image-side principal plane, which second lens images points lying in a second area sharply onto the second light-sensitive layer of the second image sensor, wherein the arrangement of the first image sensor and of the first lens is identical to the arrangement of the second image sensor and of the second lens, and wherein the arrangement of the first image sensor and of the first lens is offset relative to the arrangement of the second image sensor and of the second lens in the direction of the principal viewing axis of the device, such that the first area and the second area are spaced apart or offset in a direction parallel to the principal viewing axis of the device.

The arrangement of the first image sensor and of the first lens is identical to the arrangement of the second image sensor and of the second lens in all geometric properties and in particular also in all optical properties of the lenses. Optical or geometric properties are identical to one another if they do not differ or they differ only within the scope of series variation, tolerances and dissimilarities produced by adjustment.

Apart from the offset in the principal viewing direction, the arrangement of the first image sensor and of the first lens and the arrangement of the second image sensor and of the second lens are in particular mirror-symmetrical with respect to a plane of symmetry that contains the principal viewing axis of the device.

In the case of a device such as is described here, in particular the first lens and the first image sensor have a first depth of field range, and the second lens and the second image sensor have a second depth of field range, wherein the first depth of field range and the second depth of field range overlap.

The first depth of field range of the first lens and of the first image sensor is in particular the minimum range in the object space within which lie all points which are imaged by the first lens onto regions (also referred to as circles of least confusion or circles of confusion) within the first light-sensitive area of the first image sensor which are not larger than a light-sensitive cell of the first image sensor.

The second depth of field range of the second lens and of the second image sensor is in particular the minimum range within which lie all points which are imaged by the second lens onto regions within the second light-sensitive area of the second image sensor which are not larger than a light-sensitive cell of the second image sensor.

A light-sensitive cell or image capturing cell of an image sensor is often also referred to as a pixel. If the number of pixels represented is fewer than the number of pixels captured, the depth of field may be correspondingly larger. By way of example, if the signals of a group of 2×2 light-sensitive cells are in each case combined during the processing or conditioning of the image captured by an image sensor, a depth of field range is the range within which lie all points which are imaged by the assigned lens onto a region of the light-sensitive area of the assigned image sensor whose linear dimensions are not larger than the linear dimensions of a group of 2×2 light-sensitive cells of the assigned image sensor.

Alternatively, the depth of field range of an arrangement comprising a lens and an image sensor is the minimum range within which lie all points which are imaged by the lens onto a circle of least confusion or circle of confusion whose diameter is not more than a predetermined fraction (for example $1/1500$) of the length of the diagonal of the light-sensitive layer of the assigned image sensor.

An overlap of the depth of field ranges facilitates the fact that all objects within an enlarged range can be sharply captured by at least one of the observer and thus be perceived as sharply imaged by the observer. Said enlarged range comprises in particular a union of both depth of field ranges.

In the case of a device such as is described here, in particular at least either the first area lies within the second depth of field range or the second area lies within the first depth of field range.

In the case of a device such as is described here, in particular the first area lies within the second depth of field range and the second area lies within the first depth of field range.

In particular, the first area lies near an edge of the second depth of field range and the second area lies near an edge of the first depth of field range. An area lies near an edge of a depth of field range if it divides the depth of field range in a ratio of at least 3:1 or at least 4:1 or at least 9:1.

An overlap of the depth of field ranges in such a way that the first area lies within the second depth of field range and/or the second area lies within the first depth of field range may generate a large overlap region of the two depth of field ranges, within which overlap region both eyes of an observer can capture a sharp image, and at the same time large adjacent regions within which one eye of an observer can capture a sharp image. This may foster a pronounced spatial perception.

In the case of a device such as is described here, the depth of field ranges overlap in particular by at least half of the depth of the first depth of field range and by at least half of the depth of the second depth of field range and by at most two thirds or three quarters of the depth of the first depth of field range and by at most two thirds or three quarters of the depth of the second depth of field range.

Alternatively, the depth of field ranges may overlap for example by at least half or two thirds of the depth of the first depth of field range and by at least half or two thirds of the depth of the second depth of field range and by at most three quarters or four fifths or seven eighths of the depth of the first depth of field range and by at most three quarters or four fifths or seven eighths of the depth of the second depth of field range.

A device such as is described here furthermore comprises, in particular, a focusing unit for synchronously moving the first lens and the second lens for simultaneously moving the first area and the second area.

A movement of a lens relative to the assigned image sensor results in a movement of that area which is imaged sharply onto the image sensor by the lens. A synchronous movement of the first lens and of the second lens by the focusing unit results in a simultaneous movement of the first area, which is imaged sharply onto the first image sensor by the first lens, and of the second area, which is imaged sharply onto the second image sensor by the second lens.

A device such as is described here furthermore comprises, in particular, a slide, at which the first lens is secured rigidly or movably in a direction that is not parallel to the optical axis of the lens, and at which the second lens is secured rigidly or movably.

A device such as is described here furthermore comprises, in particular, a slide, at which the first lens is secured rigidly or movably in a direction that is not parallel to the optical axis of the lens, and at which the second lens is secured rigidly or movably, and a slide drive for moving the slide for simultaneously moving the first area and the second area.

The first lens, at the slide, is in particular rigid or movable in a direction that is orthogonal to the optical axis of the lens. A movability of the first lens relative to the slide may facilitate in particular a variation of the disparity of a stereoscopic image captured by means of the device.

The slide is movable relative to the image sensors in particular in a direction parallel to at least one of the optical axes of the lenses or parallel to the principal viewing axis of the device, in order to move the first area and the second area simultaneously by means of a single slide drive. A control or regulation overhead for coordinating two inherently mechanically independent movements with one another is thus obviated.

The device may furthermore comprise a position sensor for capturing the position of the slide. Alternatively, the slide drive may be provided and configured for capturing a position of the slide.

A device such as is described here furthermore comprises, in particular, a lens drive for moving the second lens or a part of the second lens relative to the slide and to the first lens and for moving the second area relative to the first area.

The lens drive is provided and configured in particular for moving the second lens or a part of the second lens in a direction parallel to the optical axis of the second lens.

A movement of a part of the second lens (in particular of one or more lens elements or groups of lens elements) is carried out such that in this case substantially only the second area, which is imaged sharply onto the second light-sensitive layer of the second image sensor, is moved (i.e. changes its distances from the lens and the image sensor), but the image segment is substantially not changed. The second lens is thus in particular not a pancratic system (often also referred to as zoom or varifocal lens), by means of which an image segment can be changed more than just insignificantly. The lens drive is provided and configured, in particular, to move the second lens or a part of the second lens in a direction parallel to the optical axis of the second lens.

The device may furthermore comprise a position sensor for capturing the position of the second lens or of a part of the second lens relative to the slide and/or to the first lens. Alternatively, the lens drive may be provided and configured for capturing a position of the second lens or of a part of the second lens relative to the slide and/or to the first lens.

The lens drive may facilitate a magnification or reduction or, to put it more generally, a variation of the overlap region between the first depth of field range and the second depth of field range. The lens drive may thus facilitate an adaptation of the device to the distance to the viewed object (in particular to a particularly large or to a particularly small distance), to a specific application, a specific situation or to visual habits or preferences of a user.

Without control of the lens drive, both depth of field ranges are moved simultaneously by movement of the slide.

Different functions, namely on the one hand the simultaneous movement of the first area and of the second area and thus also the simultaneous movement of both depth of field ranges, and on the other hand the variation of the overlap of the depth of field ranges, are thus realized by different drives. This may facilitate a simple and user-friendly control.

A device such as is described here furthermore comprises, in particular, a focusing unit for synchronously moving the first image sensor and the second image sensor for simultaneously moving the first area and the second area.

The focusing unit is provided and configured, in particular, to move the first image sensor parallel to the optical axis of the first lens and/or parallel to the surface normal of the first light-sensitive layer of the first image sensor. The focusing unit is furthermore provided and configured, in particular, to move the second image sensor parallel to the optical axis of the second lens and/or parallel to the surface normal of the second light-sensitive layer of the second image sensor. Alternatively or additionally, the focusing unit may be configured to move both image sensors parallel to the principal viewing axis of the device.

A device such as is described here furthermore comprises, in particular, a slide, at which the first image sensor is secured rigidly or movably in a direction that is parallel to the light-sensitive layer of the first image sensor, and at which the second image sensor is secured rigidly or movably, and a slide drive for moving the slide for simultaneously moving the first area and the second area.

A movability of the first image sensor relative to the slide may facilitate in particular a variation of the disparity of a stereoscopic image captured by means of the device.

The slide is guided in particular with little play and friction and the slide drive is provided and configured in particular so as to move the slide in a direction parallel to at least one optical axis of a lens or parallel to the principal viewing axis of the device.

The device may furthermore comprise a position sensor for capturing the position of the slide. Alternatively, the slide drive may be provided and configured for capturing a position of the slide.

If the image sensors are movable by a focusing unit or by a slide drive, the lenses may be arranged rigidly or immovably in the device or may likewise be movable relative to the device.

A device such as is described here furthermore comprises, in particular, an image sensor drive for moving the second image sensor relative to the first image sensor and for moving the second area relative to the first area.

A device such as is described here furthermore comprises, in particular, an image sensor drive for moving the second image sensor relative to the slide and to the first image sensor and for moving the second area relative to the first area.

The image sensor drive is provided and configured in particular for moving the second image sensor relative to the first image sensor and/or relative to the slide in a direction parallel to the optical axis of the second lens and/or parallel to the surface normal of the light-sensitive layer of the second image sensor and/or parallel to the principal viewing axis of the device.

The device may furthermore comprise a position sensor for detecting the position of the second image sensor relative to the slide and/or to the first image sensor. Alternatively, the image sensor drive may be provided and configured for capturing a position of the second image sensor relative to the slide and/or to the first image sensor.

A method for adjusting a device for capturing a stereoscopic image signal during production or maintenance of the device comprises a step of adjusting at least one of a first lens and a first image sensor of the device in such a way that the first lens generates a sharp image of a first object at the first image sensor, and a step of adjusting at least one of a second lens and a second image sensor of the device in such a way that the second lens generates a sharp image of a second object at the second image sensor, wherein the first object lies in a first predetermined plane, wherein the second object lies in a second predetermined plane, wherein the first plane and the second plane are in each case orthogonal to a principal viewing axis of the device, and wherein the first predetermined plane and the second predetermined plane are parallel to one another and spaced apart from one another.

The method is able to be performed in particular by a device such as is described here. In particular a device such as is described here is adjustable by means of the method.

A method such as is described here furthermore comprises, in particular, a step of arranging an adjustment gauge with the first object and with the second object at a predetermined position relative to the device in such a way that the first object is arranged in the first predetermined plane and the second object is arranged in the second predetermined plane.

The step of arranging an adjustment gauge is performed before the step of adjusting at least one of the first lens and the first image sensor and before the step of adjusting at least one of the second lens and the second image sensor.

A method such as is described here furthermore comprises, in particular, a step of fixing at least either the image sensors relative to one another or the lenses relative to one another.

The step of fixing is performed after the steps of adjusting.

The step of adjusting at least one of the first lens and the first image sensor is performed in particular by adjusting a slide, at which either the first lens or the first image sensor is rigidly secured. The step of adjusting at least one of the second lens and the second image sensor is performed in particular after the step of adjusting at least one of the first lens and the first image sensor. The step of adjusting at least one of the second lens and the second image sensor is performed in particular by adjusting the second lens relative to the first lens and/or to a slide at which the first lens is rigidly secured, or by adjusting the second image sensor relative to the first image sensor and/or relative to a slide at which the first image sensor is rigidly secured.

After the device has been adjusted by the method described, the device can be used. In the envisaged use of the device, both lenses may be moved synchronously (in particular together with a slide at which the lenses are secured). Alternatively, in the envisaged use of the device, both image sensors may be moved synchronously (in particular together with a slide at which the image sensors are secured). The synchronous movement may be effected manually or by means of a motor that is controlled manually or by a control unit. With a synchronous movement of both lenses or of both image sensors, the first area, which is imaged sharply into the light-sensitive layer of the first image sensor by the first lens, and the second area, which is imaged sharply into the light-sensitive layer of the second image sensor by the second lens, may be moved simultaneously.

A control unit for controlling a motor-based synchronous movement of both image sensors or of both lenses may facilitate an automatic focusing—for example on the basis of determining an edge contrast.

BRIEF DESCRIPTION OF THE DRAWINGS

Embodiments are explained in greater detail below with reference to the accompanying figures, in which:

FIG. 5 shows a schematic illustration of optical imagings in a further device for capturing a stereoscopic image;

FIG. 6 shows a schematic illustration of optical imagings in a further device for capturing a stereoscopic image;

DETAILED DESCRIPTION

Figure 1:
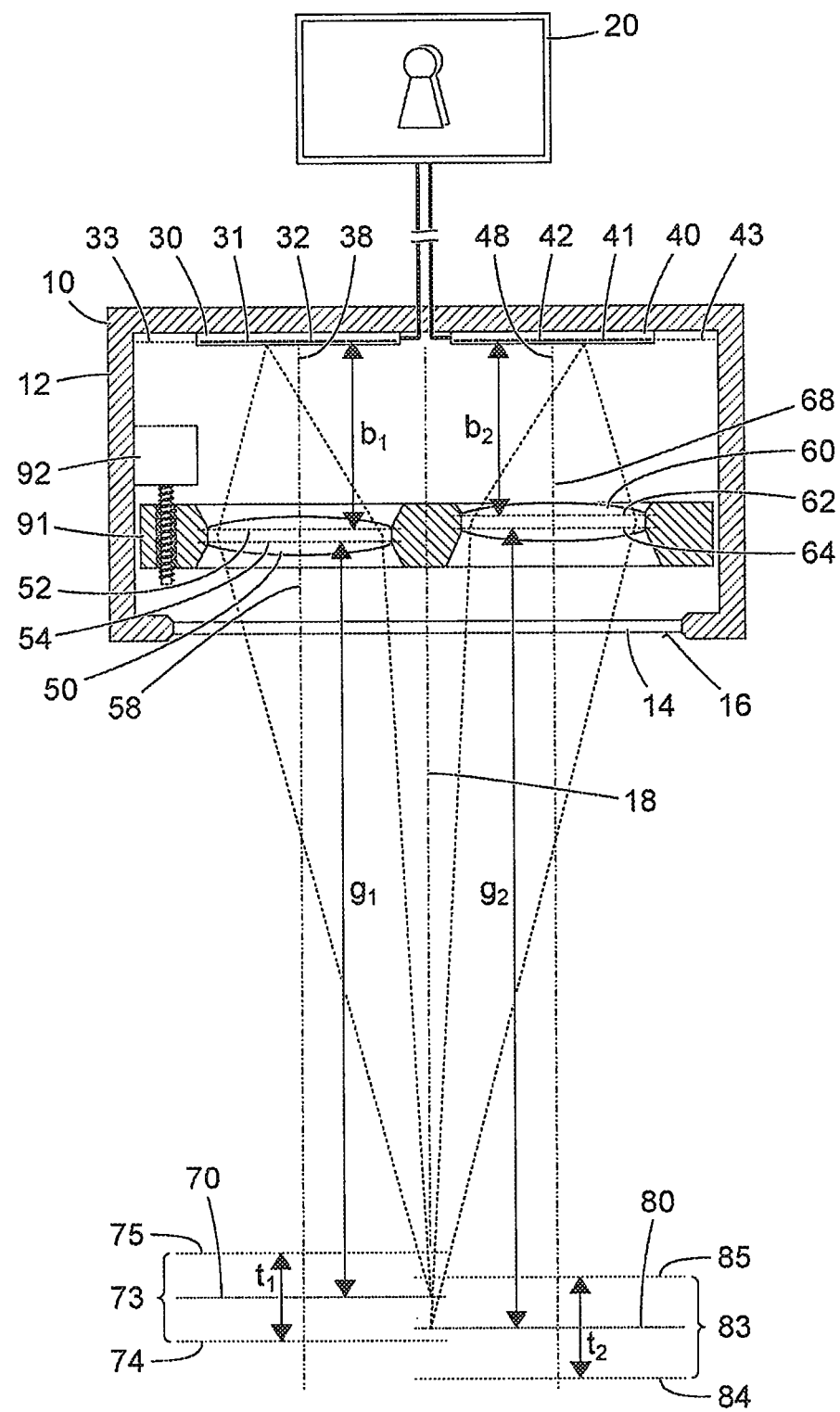
FIG. 1 shows a schematic illustration of a device for capturing a stereoscopic image.

FIG. 1 shows a schematic illustration of a device 10 for capturing a stereoscopic image. Some parts of the device 10 are illustrated in a sectional view along a sectional plane. In this respect, the illustration in FIG. 1 has in part the character of a sectional illustration. Some sectional areas are provided with hatching. Other sectional areas, for example of components composed of optically transparent materials, are illustrated without hatching.

The device 10 comprises a housing 12 having an opening closed by a window component 14. The window component 14 is formed from a material that is transparent to light at least within the wavelength range visible to the healthy human eye. The housing 12 comprising the window component 14 may be fluid-tight, optionally hermetically tight. An outer (in FIG. 1: lower) surface of the window component 14 forms a light entrance area 16, through which light emanating from an object to be observed can enter the housing 12 and the device 10.

The device 10 has a principal viewing direction and principal viewing axis 18. The principal viewing axis 18 of the device 10 lies in the center of the region within which may lie all objects from which the device 10 can capture a stereoscopic image.

The device 10 is coupled to a reproduction device 20 for reproducing a stereoscopic image captured by the device 10. The reproduction device 20 comprises for example a projector and a projection surface or one or more screens for the simultaneous or rapidly alternating representation of the images—provided for the left eye and for the right eye of an observer—of a stereoscopic image captured by the device 10. The reproduction device 20 may be part of the device 10 or may be combined with the device 10 to form a system.

The device 10 comprises a first image sensor 30 for capturing an image provided for a first (for example left) eye of an observer and a second image sensor 40 for capturing an image provided for a second (for example right) eye of the observer. The image sensors 30, 40 are for example CCD or CMOS sensors. The image sensors 30, 40 are configured to generate (in particular electrical) analog or digital image signals representing the images captured by the image sensors 30, 40. Image signals generated by the image sensors 30, 40 may be amplified, conditioned and/or processed and then stored by units not illustrated in FIG. 1 and/or may be reproduced by the reproduction device 20 or in some other way.

Each image sensor 30, 40 comprises a multiplicity of pixels or image capturing cells or light-sensitive cells 31, 41. The light-sensitive cells 31, 41 are arranged in light-sensitive layers 32, 42. In the example illustrated, the light-sensitive layers 32, 42 of the image sensors 30, 40 are planar in each case. Since the light-sensitive layers 32, 42 of the image sensors 30, 40 are very thin in each case, reference is made hereinafter to planes 33, 43 in which the light-sensitive layers 32, 42 of the image sensors 30, 40 lie. A more precise definition of the planes 33, 43 is that they intersect the light-sensitive layers 32, 42 of the image sensors 30, 40 centrally, such that in each case half of all the elementary events contributing to the optoelectronic image conversion take place upstream and downstream of the plane 33, 43. Furthermore, reference is made hereinafter to surface normals 38, 48 of the planes 33, 43 in which the light-sensitive layers 32, 42 of the image sensors 30, 40 lie.

In FIG. 1, the image sensors 30, 40 are indicated as components which are separate and spaced apart from one another. Alternatively and in a departure from the illustration in FIG. 1, both image sensors 30, 40 may be realized in a single common component, for example as two different (and in particular spatially spaced-apart) regions of a continuous light-sensitive layer of a semiconductor component.

The device 10 furthermore comprises a first lens 50, which is assigned to the first image sensor 30, and a second lens 60, which is assigned to the second image sensor 40. Each lens 50, 60 has an image-side principal plane 52, 62, an object-side principal plane 54, 64 and an optical axis 58, 68. The principal planes used in the context of the working model of paraxial optics for describing the refraction of light by the lenses 50, 60 are regarded as principal planes. Each lens 50, 60 may comprise one or more lens elements having curved light-refracting surfaces and/or an inhomogeneous refractive index, reflective surfaces and/or light-diffracting or other optical elements. In FIG. 1, each lens 50, 60 is represented by way of example by a single lens element.

In the example shown in FIG. 1, the principal planes 52, 54, 62, 64 of the lenses 50, 60 are parallel to the planes 33, 43 in which the light-sensitive layers 32, 42 of the image sensors 30, 40 lie. Therefore, the optical axes 58, 68 of the lenses 50, 60 are simultaneously surface normals 38, 48 of the planes 33, 43 in which the light-sensitive layers 32, 42 of the image sensors 30, 40 lie.

The first lens 50—apart from diffraction at the edge of the first lens 50 and imaging aberrations—images points in a first area 70 sharply (apart from imaging aberrations: in a punctiform fashion) into the light-sensitive layer 32 of the first image sensor 30. The greater the distance between a point in the object space and the first area 70, the larger the region within the light-sensitive layer 32 of the first image sensor 30 in which light that emanates from the point and is refracted by the first lens 50 is incident. This region is also referred to as the circle of least confusion or circle of confusion. A first depth of field range 73 of the arrangement comprising the first image sensor 30 and the first lens 50, as shown in FIG. 1, is the minimum range of the object space within which lie all points whose images generated by the first lens 50 in the light-sensitive layer 32 of the first image sensor 30 are not larger than a light-sensitive cell 31 of the first image sensor 30. The first depth of field range 73 extends from a far limit or a distal edge 74 to a near limit or a proximal edge 75.

In the example illustrated, the first area 70 and the edges 74, 75 of the first depth of field range 73 are in each case planar or substantially planar and parallel to the principal planes 52, 54 of the first lens 50 and to the plane 33 in which the light-sensitive layer 32 of the first image sensor 30 lies. The depth $t_1$ of the first depth of field range 73 is dependent on the size of the individual light-sensitive cells 31 of the first image sensor 30 and on properties (in particular the size of the aperture stop) of the first lens 50.

The distance between the first area 70 and the object-side principal plane 54 of the first lens 50 is referred to as the object distance $g_1$. The distance between the plane 33 in which the light-sensitive layer 32 of the first image sensor 30 lies and the image-side principal plane 52 of the first lens 50 is referred to as the image distance $b_1$.

The second lens 60—apart from diffraction at the edge of the second lens 60 and imaging aberrations—images points in a second area 80 sharply (apart from imaging aberrations: in a punctiform fashion) into the light-sensitive layer 42 of the second image sensor 40. The greater the distance between a point in the object space and the second area 80, the larger the region within the light-sensitive layer 42 of the second image sensor 40 in which light that emanates from the point and is refracted by the second lens 60 is incident. A second depth of field range 83 of the arrangement comprising the second image sensor 40 and the second lens 60, as shown in FIG. 1, is the minimum range of the object space within which lie all points whose images generated by the second lens 60 in the light-sensitive layer 42 of the second image sensor 40 are not larger than a light-sensitive cell 41 of the second image sensor 40. The second depth of field range 83 extends from a far limit or a distal edge 84 to a near limit or a proximal edge 85.

In the example illustrated, the second area 80 and the edges 84, 85 of the second depth of field range 83 are in each case planar or substantially planar and parallel to the principal planes 62, 64 of the second lens 60 and to the plane 43 in which the light-sensitive layer 42 of the second image sensor 40 lies. The depth $t_2$ of the second depth of field range 83 is dependent on the size of the individual light-sensitive cells 41 of the second image sensor 40 and on properties (in particular the size of the aperture stop) of the second lens 60.

The distance between the second area 80 and the object-side principal plane 64 of the second lens 60 is referred to as the object distance $g_2$. The distance between the plane 43 in which the light-sensitive layer 42 of the second image sensor 40 lies and the image-side principal plane 62 of the second lens 60 is referred to as the image distance $b_2$.

In the case of the device 10 shown in FIG. 1, the lenses 50, 60 have identical optical properties, in particular identical focal lengths, within the manufacturing tolerance, and the image distances $b_1$ and $b_2$ differ. The object distances $g_1$ and $g_2$ are correspondingly different as well. The planes 33 in which the light-sensitive layer 32 of the first image sensor 30 lies is identical to the plane 43 in which the light-sensitive layer 42 of the second image sensor 40 lies. The first area 70, which is imaged sharply into the light-sensitive layer 32 of the first image sensor 30 by the first lens 50, is spaced apart from the second area 80, which is imaged sharply into the light-sensitive layer 42 of the second image sensor 40 by the second lens 60. The depth of field ranges 73, 83 overlap one another in such a way that the first area 70, which is imaged sharply into the light-sensitive layer 32 of the first image sensor 30 by the first lens 50, lies within the second depth of field range 83 of the second lens 60 and of the second image sensor 40, and that the second area 80, which is imaged sharply into the light-sensitive layer 42 of the second image sensor 40 by the second lens 60, lies within the first depth of field range 73 of the first lens 50 and of the first image sensor 30.

The first lens 50 and the second lens 60 are arranged alongside one another in a slide 91 and are in each case rigidly connected to the side 91. A drive 92 is provided and configured to move the slide 91 in a direction parallel to the principal viewing axis 18 of the device 10. When the drive 92 moves the slide 91 with the lenses 50, 60, the image distances $b_1$, $b_2$ and correspondingly the object distances $g_1$, $g_2$ are changed simultaneously. In this case, the difference between the image distances $b_1$, $b_2$ remains constant by virtue of the rigid arrangement of the lenses 50, 60 in the slide 91.

The overlap of the first depth of field range 73 of the arrangement comprising the first lens 50 and the first image sensor 30 and of the second depth of field range 83 of the arrangement comprising the second lens 60 and the second image sensor 40 gives rise to an enlarged overall region within which at least one of the two captured images is sharp. A core region, which corresponds to the intersection of both depth of field ranges 73, 83 and in which both images are sharp, is adjoined in both directions by regions in which one of the two captured images is sharp. The region within which objects are perceived as sharply imaged by a human observer and the region within which a spatial impression arises are therefore larger than in the case of identical areas 73, 83.

Figure 2:
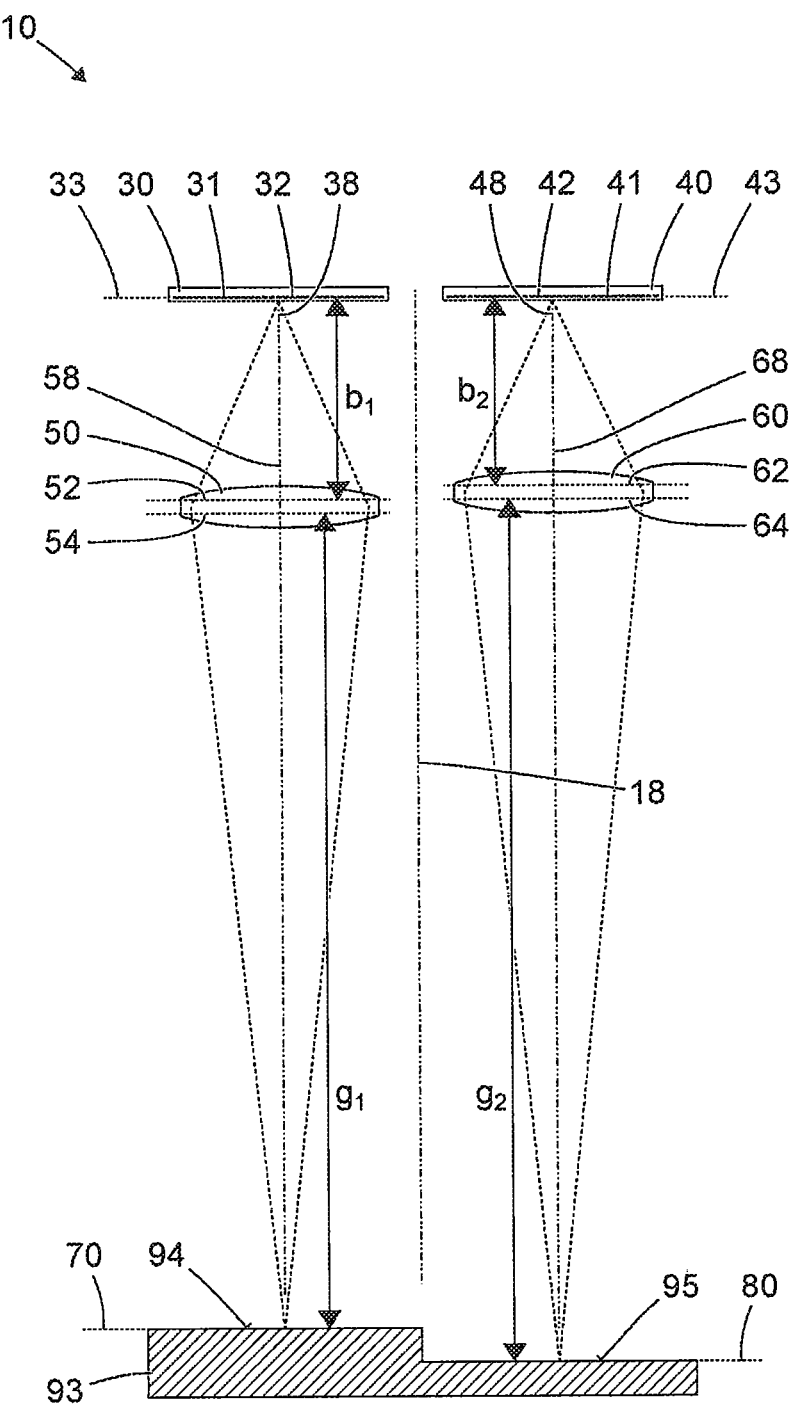
FIG. 2 shows a schematic illustration of optical imagings in a device for capturing a stereoscopic image.

FIG. 2 shows a schematic illustration only of the components of the device 10 from FIG. 1 which are directly involved in the optical imaging of objects. For the rest, the illustration in FIG. 2 is similar to the illustration in FIG. 1.

FIG. 2 shows a situation at the end of an adjusting method for adjusting both beam paths. For this purpose, an adjustment gauge 93 is arranged at a predetermined position relative to the device 10. The adjustment gauge comprises a first area 94 and a second area 95. The areas 94, 95 at the adjustment gauge 93 extend along two planes which are parallel and spaced apart from one another. High-contrast structures are in each case provided at the areas 94, 95 at the adjustment gauge 93.

In the case of the arrangement of the adjustment gauge 93 as provided and illustrated in FIG. 2, the planes along which the areas 94, 95 of the adjustment gauge 93 extend are orthogonal to the principal viewing axis 18 of the device 10. In the case of the arrangement of the adjustment gauge 93 as provided and shown in FIG. 2, the optical axis 58 of the first lens 50 intersects the first area 94 at the adjustment gauge 93, and the optical axis 68 of the second lens 60 intersects the second area 95 at the adjustment gauge 93.

After the adjustment gauge 93 has been arranged at the position provided and shown in FIG. 2, the first lens 50 is positioned (in particular by movement of the slide 91—cf. FIG. 1) such that the first lens 50 images the first area 94 at the adjustment gauge 93 (apart from imaging aberrations) sharply into the light-sensitive layer 32 of the first image sensor 30, that is to say that the first area 70 (cf. the description of FIG. 1) coincides with the first area 94 at the adjustment gauge. This is done in particular by displacing the slide 91 (cf. FIG. 1), at which the first lens 50 is rigidly secured.

Afterward, without a further movement of the slide 91 and of the first lens 50, the second lens 60 is adjusted, in particular positioned, such that the second lens 60 images the second area 95 at the adjustment gauge 93 sharply into the light-sensitive layer 42 of the second image sensor 40, that is to say that the second area 80 (cf. the description of FIG. 1) coincides with the second area 95 at the adjustment gauge. This is done in particular by displacing the second lens 60, which is not yet rigidly secured at the slide 91 at this point in time, relative to the slide 91 (cf. FIG. 1).

If the first lens 50 images the first area 94 at the adjustment gauge 93 sharply into the light-sensitive layer 32 of the first image sensor 30 and, simultaneously, the second lens 60 images the second area 95 at the adjustment gauge 93 sharply into the light-sensitive layer 42 of the second image sensor 40, the second lens 60 is fixed relative to the first lens 50. This is done, in particular, by virtue of the second lens 60 being rigidly connected—for example by means of an adhesive or a clamp—to the slide 91 (cf. FIG. 1).

Figure 3:
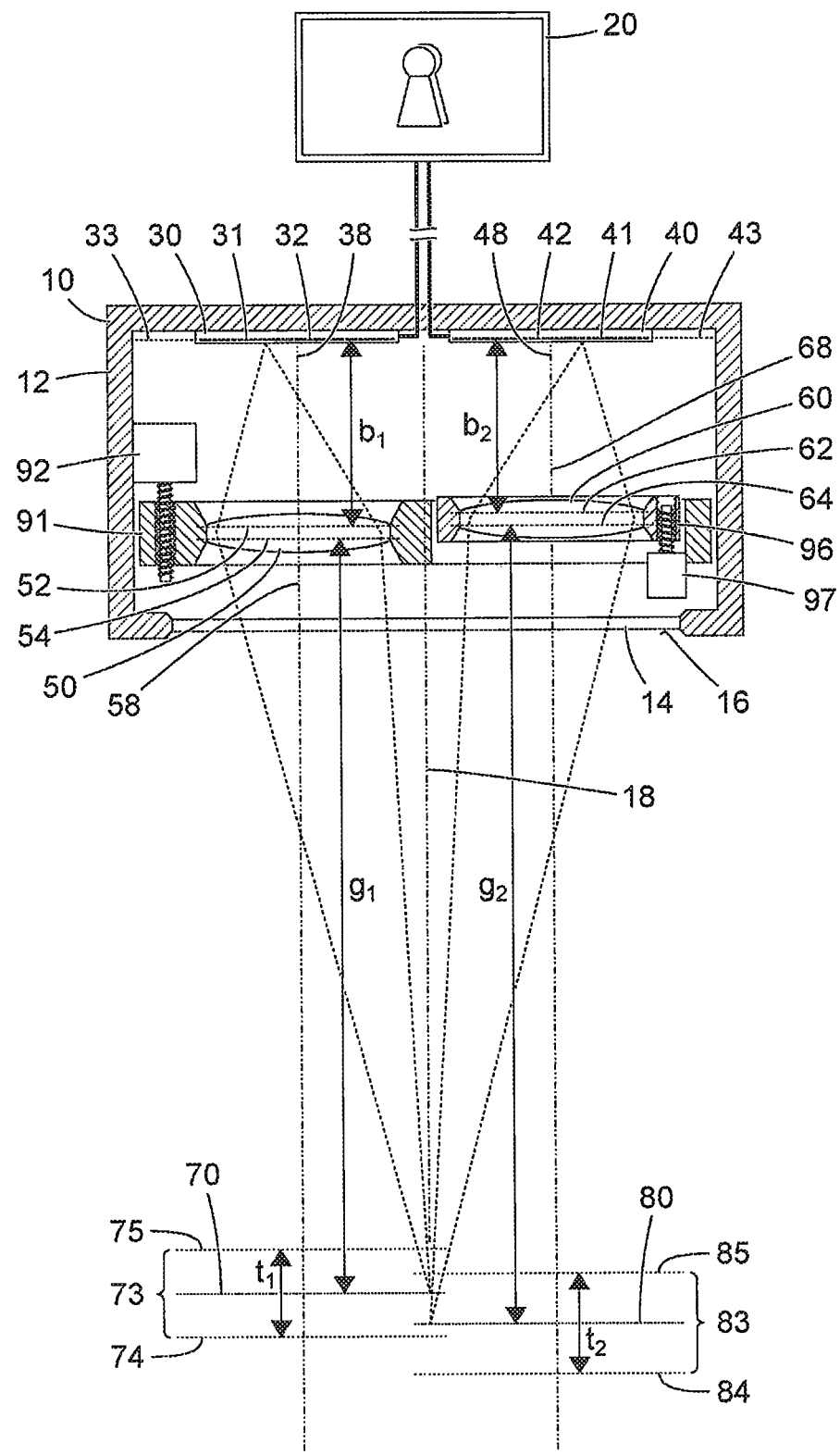
FIG. 3 shows a schematic illustration of a further device for capturing a stereoscopic image.

FIG. 3 shows a schematic illustration of a further device 10 for capturing a stereoscopic image, which in some features, properties and functions is similar to the device illustrated with reference to FIGS. 1 and 2. The manner of illustration in FIG. 3 corresponds to that in FIG. 1. A description is given below of, in particular, features, properties and functions of the device 10 shown in FIG. 3 in which said device differs from the device illustrated with reference to FIGS. 1 and 2.

The device 10 shown in FIG. 3 differs from the device illustrated with reference to FIGS. 1 and 2 in particular in that the second lens 60 is not rigidly connected to the first lens 50. Instead, a small slide 96 is provided in addition to the large slide 91, which is movable by a first drive 92. The small slide 96 is rigidly connected to the second lens 60. A second drive 97 is provided and configured to move the second slide 96 relative to the first slide 91.

The second drive 97 may be used exclusively during the adjustment process illustrated with reference to FIG. 2. Alternatively or additionally, during the envisaged use of the device 10, the small slide 96 and the second lens 60 may be moved relative to the large slide 91 and the first lens 50 by means of the second drive 97. By virtue of the movement of the small slide 96 and of the second lens 60 relative to the large slide and the first lens 50, the second area 80 and the second depth of field range 83 may be moved relative to the first area 70 and to the first depth of field range 73. At the same time, the overlap between the depth of field ranges 73, 83 is thus varied. The overlap between the depth of field ranges 73, 83 may be varied for adaptation to the visual habits or preferences of a user, to a specific application situation and/or to the distance of a viewed object from the device 10.

In the case of the devices 10 illustrated with reference to FIGS. 1 to 3, the planes 33, 43 in which the light-sensitive layers 32, 42 of the image sensors 30, 40 lie are identical. Alternatively and in a departure from the illustrations in FIGS. 1 to 3, the planes 33, 43 in which the light-sensitive layers 32, 42 of the image sensors 30, 40 lie may be parallel and spaced apart from one another.

Figure 4:
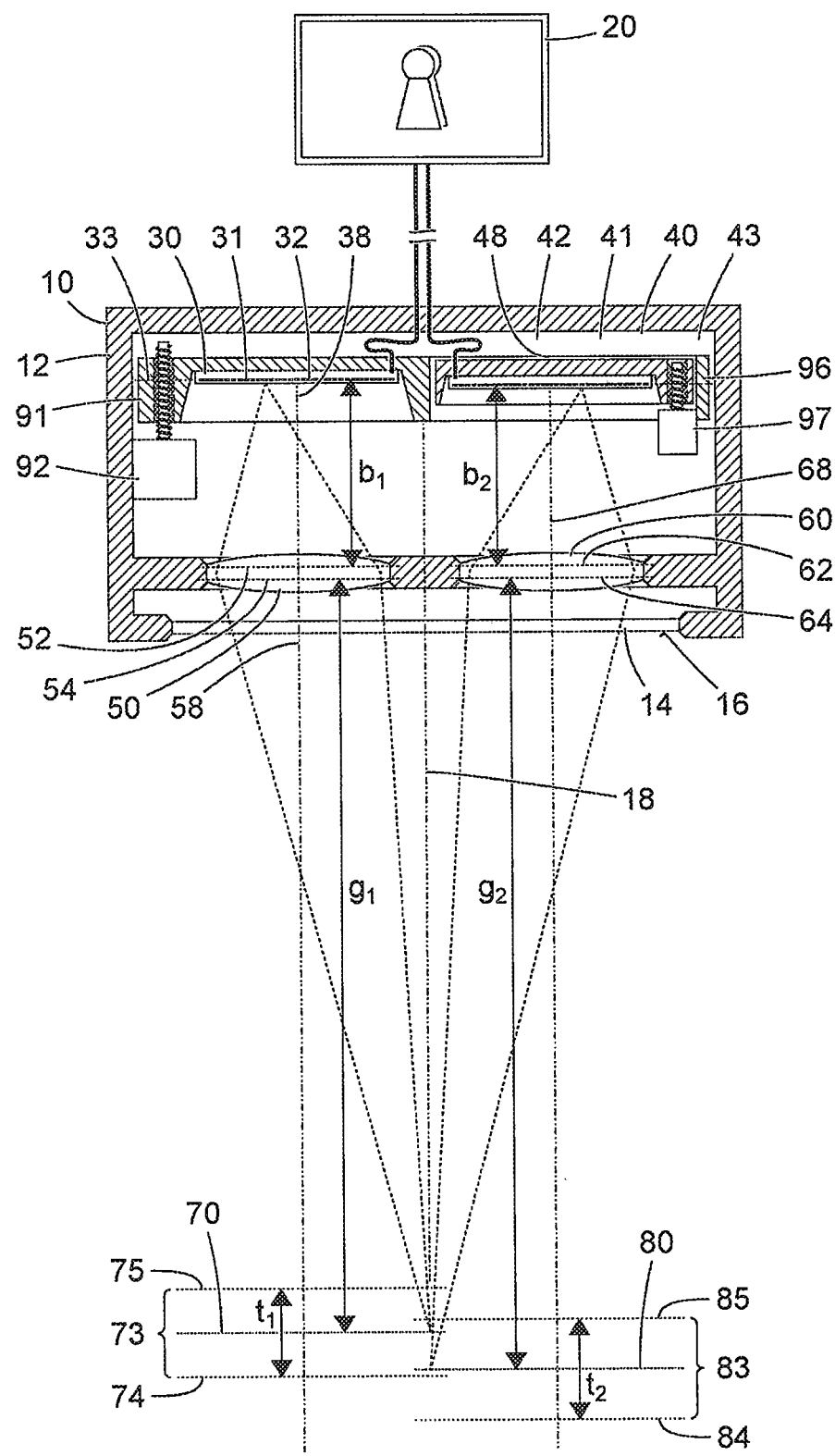
FIG. 4 shows a schematic illustration of a further device for capturing a stereoscopic image.

FIG. 4 shows a schematic illustration of a further device 10 for capturing a stereoscopic image, which in some features, properties and functions is similar to the device illustrated with reference to FIGS. 1 to 3. The manner of illustration in FIG. 4 corresponds to that in FIGS. 1 and 3. A description is given below of, in particular, features, properties and functions of the device 10 in which said device differs from the devices illustrated with reference to FIGS. 1 to 3.

The device 10 shown in FIG. 4 differs from the devices illustrated with reference to FIGS. 1 to 3 in particular in that the lenses 50, 60 are rigidly connected to the housing 12 and the image sensors 30, 40 are movable relative to the housing 12. The first image sensor 30 is rigidly secured at a large slide 91, which is movable relative to the housing 12 of the device 10 and thus in particular relative to the first lens 50 by means of a first drive 92. The second image sensor 40 is rigidly secured at a small slide 96, which is movable relative to the large slide 91 by means of a second drive 97.

By means of the first drive 92, the slide 91 and the image sensors 30, 40 can be moved simultaneously, as a result of which the areas 70, 80 that are imaged sharply onto the image sensors 30, 40 by the lenses 50, 60 are moved simultaneously. The small slide 96 and with it the second image sensor 40 can be moved relative to the large slide 91 by the second drive 97 in order to move the second area 80, which is imaged sharply onto the second image sensor 40 by the second lens 60, relative to the first area 70, which is imaged sharply onto the first image sensor 30 by the first lens 50.

In the case of the example shown in FIG. 4, the object-side principal planes 54, 64 of the lenses 50, 60 are identical and the image-side principal planes 52, 62 of the lenses 50, 60 are identical. Alternatively and in a departure from the illustration in FIG. 4, the object-side principal planes 54, 64 of the lenses 50, 60 may be spaced apart from one another and the image-side principal planes 52, 62 of the lenses 50, 60 may be spaced apart from one another.

Alternatively and in a departure from the illustration in FIG. 4, with omission of the small slide 96 and of the second drive 97, both image sensors 30 may be rigidly connected to the large slide 91. In this case, the planes 33, 43 in which the light-sensitive layers 32, 42 of the image sensors 30, 40 lie may be parallel and spaced apart from one another or, if the principal planes 52, 62, 54, 64 of the lenses 50, 60 do not coincide, in a departure from the illustration in FIG. 4, may be identical.

In the case of the devices 10 illustrated with reference to FIGS. 3 and 4, there exists a clear functional separation between the drives 92, 97. The first drive 92 is provided in each case for the joint movement of the areas 70, 80 and of the depth of field ranges 73, 83; the second drive 97 is provided in each case for the movement of the second area 80 relative to the first area 70 and thus also of the second depth of field range 83 relative to the first depth of field range 73.

FIG. 5 shows a schematic illustration of parts of a further device 10 for capturing a stereoscopic image, which in some features, properties and functions is similar to the devices illustrated with reference to FIGS. 1 to 4. The manner of illustration corresponds to that of the illustration in FIG. 2. In particular, only components of the device 10 that are directly involved in the optical imaging of objects are illustrated, namely the lenses 50, 60 and the image sensors 30, 40. A description is given below of, in particular, features, properties and functions of the device 10 shown in FIG. 5 in which said device differs from the devices illustrated with reference to FIGS. 1 to 4.

The device 10 shown in FIG. 5 differs from the devices illustrated with reference to FIGS. 1 to 4 in particular in that the optical axes 58, 68 of the lenses 50, 60 are not arranged parallel to one another and to the principal viewing axis 18 of the device 10. Rather, the optical axes 58, 68 of the lenses 50, 60 intersect the principal viewing axis 18 of the device 10 at a point outside the spatial region illustrated. Correspondingly, the image-side principal planes 52, 62 of the lenses 50, 60 are also not parallel to one another, but rather intersect one another in a straight line of intersection. In the example illustrated, said line of intersection is orthogonal to the plane of the drawing in FIG. 5. Correspondingly, the object-side principal planes 54, 64 of the lenses 50, 60 are also not parallel to one another, but rather intersect one another in a straight line of intersection. In the example illustrated, said line of intersection is also orthogonal to the plane of the drawing in FIG. 5.

The planes 33, 43 in which the light-sensitive layers 32, 42 of the image sensors 30, 40 are arranged are not parallel to the principal planes 52, 54, 62, 64 of the lenses 50, 60 and not orthogonal to the optical axes 58, 68 of the lenses 50, 60. The distance between the first image sensor 30 and the image-side principal plane 52 of the first lens 50, i.e. the image distance $b_1$ for an object lying on the optical axis 58 of the first lens 50, is the distance between the point of intersection of the plane 33 in which the light-sensitive layer 32 of the first image sensor 30 lies with the optical axis 58 of the first lens 50 and the point of intersection of the image-side principal plane 52 of the first lens 50 with the optical axis 58 of the first lens 50. The distance between the second image sensor 40 and the image-side principal plane 62 of the second lens 60, i.e. the image distance $b_2$ for an object lying on the optical axis 68 of the second lens 60, is the distance between the point of intersection of the plane 43 in which the light-sensitive layer 42 of the second image sensor 40 lies with the optical axis 68 of the second lens 60 and the point of intersection of the image-side principal plane 62 of the second lens 60 with the optical axis 68 of the second lens 60. Since the planes 33, 43 in which the light-sensitive layers 32, 42 of the image sensors 30, 40 lie are identical and the image distances $b_1$, $b_2$ are different, the line of intersection between the image-side principal planes 52, 62 of the lenses 50, 60 lies asymmetrically, that is to say does not intersect the principal viewing axis 18 of the device 10, but rather is spaced apart from the latter.

Alternatively and in a departure from the illustration in FIG. 5, the planes 33, 43 in which the light-sensitive layers 32, 42 of the image sensors 30, 40 lie may be parallel and spaced apart from one another. In this case, the line of intersection between the image-side principal planes 52, 62 of the lenses 50, 60 may intersect the principal viewing axis 18 of the device 10.

FIG. 6 shows a schematic illustration of a further device 10 for capturing a stereoscopic image, which in some features, properties and functions is similar to the devices illustrated with reference to FIGS. 1 to 5. The manner of illustration in FIG. 6 corresponds to that of the illustration in FIG. 5. A description is given below of, in particular, features, properties and functions in which the device 10 shown in FIG. 6 differs from the devices illustrated with reference to FIGS. 1 to 5.

In the case of the device 10 shown in FIG. 6, the image-side principal planes 52, 62 of the lenses 50, 60 are identical, and the object-side principal planes 54, 64 of the lenses 50, 60 are identical. The optical axes 58, 68 of the lenses 50, 60 are parallel to one another and parallel to the principal viewing axis 18 of the device 10. The planes 33, 43 in which the light-sensitive layers 32, 42 of the image sensors 30, 40 lie are not orthogonal to the optical axes 58, 68 of the lenses 50, 60 and not parallel to one another. The image distances $b_1$, $b_2$ are different. In the example illustrated, the surface normals of the planes 33, 43 in which the light-sensitive layers 32, 42 of the image sensors 30, 40 lie form identical angles with the optical axes 58, 68 of the lenses 50, 60. The planes 33, 43 in which the light-sensitive layers 32, 42 of the image sensors 30, 40 lie intersect in a straight line of intersection. In the example illustrated, said line of intersection is orthogonal to the plane of the drawing in FIG. 6. Said line of intersection does not intersect the principal viewing axis 18 of the device 10, but rather is spaced apart from the latter.

Alternatively and in a departure from the illustration in FIG. 6, the image-side principal planes 52, 62 of the lenses 50, 60 may differ from one another, in particular be parallel to and spaced apart from one another. In this case, the line of intersection between the planes 33, 43 in which the light-sensitive layers 32, 42 of the image sensors 30, 40 lie may intersect the principal viewing axis 18 of the device 10.

Figure 7:
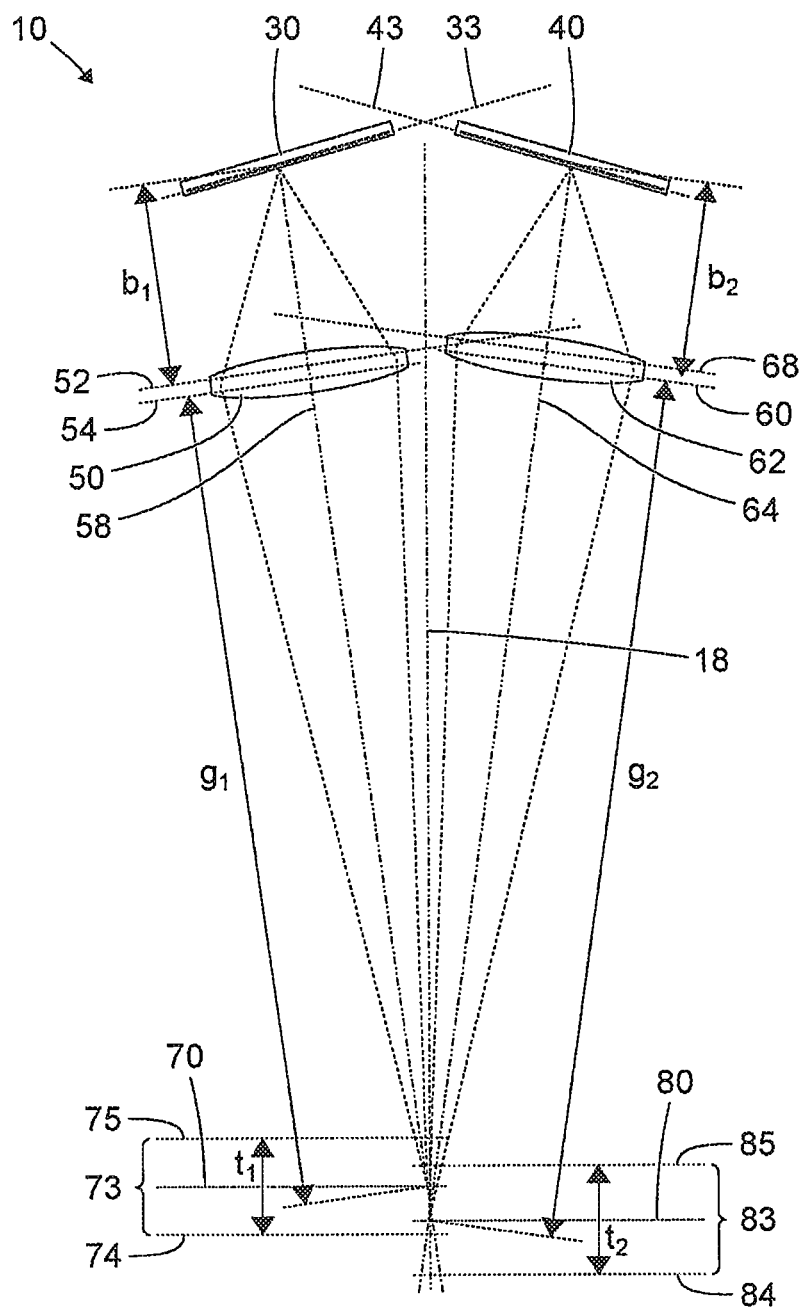
FIG. 7 shows a schematic illustration of optical imagings in a further device for capturing a stereoscopic image.

FIG. 7 shows a schematic illustration of a further device 10, which in some features, properties and functions is similar to the devices illustrated with reference to FIGS. 1 to 6. The manner of illustration corresponds to that of the illustrations in FIGS. 5 and 6. A description is given below of, in particular, features, properties and functions in which the device 10 shown in FIG. 7 differs from the devices illustrated with reference to FIGS. 1 to 6.

The device 10 shown in FIG. 7 differs from the devices illustrated with reference to FIGS. 1 to 6 in particular in that—in a manner similar to that in the case of the device illustrated with reference to FIG. 5—the optical axes 58, 68 of the lenses 50, 60 are not parallel to one another, but rather intersect one another, and that at the same time the planes 33, 43 in which the light-sensitive layers 32, 42 of the image sensors 30, 40 lie are not parallel to one another, but rather—in a manner similar to that in the case of the device illustrated with reference to FIG. 6—intersect in a straight line of intersection. In the example illustrated, said line of intersection is orthogonal to the plane of the drawing in FIG. 7. Correspondingly, the image-side principal planes 52, 62 of the lenses 50, 60 also intersect in a straight line of intersection. In the example illustrated, said line of intersection is also orthogonal to the plane of the drawing in FIG. 7. The image distances $b_1$, $b_2$ differ.

Figure 8:
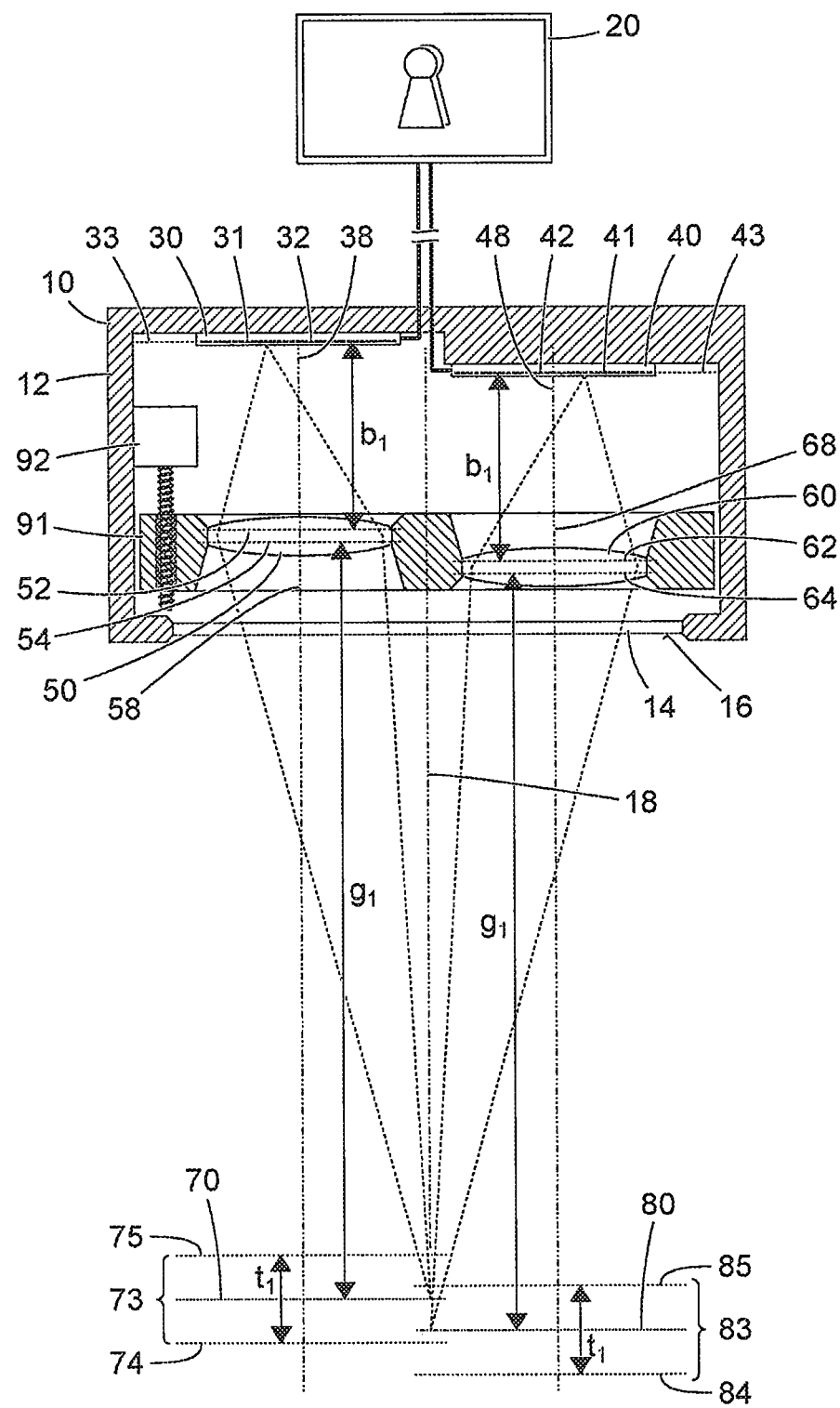
FIG. 8 shows a schematic illustration of a further device for capturing a stereoscopic image.

FIG. 8 shows a schematic illustration of a further device 10 for capturing a stereoscopic image, which in some features, properties and functions is similar to the devices illustrated with reference to FIGS. 1 to 7, and particularly the device illustrated with reference to FIGS. 1 and 2. The manner of illustration in FIG. 8 is similar to the manner of illustration in FIGS. 1, 3 and 4. A description is given below of, in particular, features, properties and functions of the device 10 in which said device differs from the device illustrated with reference to FIGS. 1 and 2.

The device 10 shown in FIG. 8 differs from the device illustrated with reference to FIGS. 1 and 2 in particular in that not only both lenses 50, 60 but also both image sensors 30, 40 are arranged offset relative to one another in a direction parallel to the principal viewing axis 18. The second image sensor 40 is arranged offset relative to the first image sensor 30 by the same distance by which the second lens 60 is also arranged offset relative to the first lens 50. The arrangement comprising the first image sensor 30 and the first lens 50 and the arrangement comprising the second image sensor 40 and the second lens 60 therefore have the same image distance $b_1$.

Both lenses 50, 60 are—within the scope of manufacturing tolerances or series variation—identical or have at least the same focal length. Therefore, the arrangement comprising the first image sensor 30 and the first lens 50 and the arrangement comprising the second image sensor 40 and the second lens 60 also have the same object distance $g_1$. Correspondingly, the areas 70, 80 which are imaged sharply into the light-sensitive layers 32, 42 of the image sensors 30, 40 by the lenses 50, 60 are offset by the same distance by which the image sensors 30, 40 and the lenses 50, 60 are offset relative to one another.

However, the distance by which the second image sensor 40 is offset relative to the first image sensor 30 and the second lens 60 is offset relative to the first lens 50 and the second area 80 is offset relative to the first area 70 is chosen such that the depth of field ranges 73, 83 overlap.

Alternatively and in a departure from the illustration in FIG. 8, in the case of the device 10—for example in a manner similar to that in the case of the embodiments illustrated with reference to FIGS. 3 and 4—the second lens 60 may be movable relative to the first lens 50 and/or the second image sensor 40 may be movable relative to the first image sensor 30.

Alternatively and in a departure from the illustration in FIG. 8, in the case of the device 10—for example in a manner similar to that in the case of the embodiments illustrated with reference to FIGS. 5 to 7—the planes 33, 43 in which the light-sensitive layers 32, 42 of the image sensors 30, 40 lie and/or the principal planes 52, 54, 62, 64 of the lenses 50, 60 may not be arranged orthogonally to the principal viewing axis 18, but rather at an inclination. In this case, however, the arrangement comprising the first image sensor 30 and the first lens 50 and the arrangement comprising the second image sensor 40 and the second lens 60—apart from the offset in a direction parallel to the principal viewing axis 18—are in particular mirror-symmetrical with respect to one another.

Figure 9:
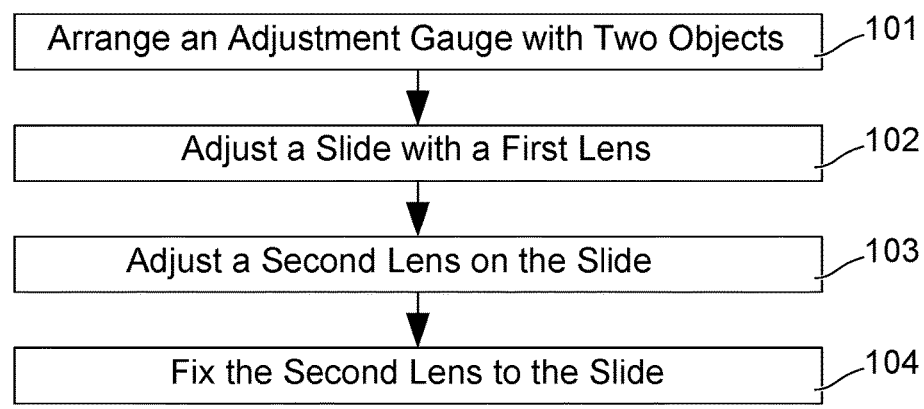
FIG. 9 shows a schematic flow diagram of a method for adjusting a device for capturing a stereoscopic image.

FIG. 9 shows a schematic flow diagram of a method for adjusting a device for capturing a stereoscopic image. The method is applicable, in particular, to the devices 10 illustrated with reference to FIGS. 1 to 8. However, the method is also applicable to devices which differ from the devices illustrated with reference to FIGS. 1 to 8. Nevertheless, reference signs from FIGS. 1 to 8 are used below in order to simplify an understanding of the method.

A first step 101 involves arranging an adjustment gauge 93 having a first area 94 and a second area 95 in a predetermined position and orientation relative to the device 10 to be adjusted. The first area 94 and the second area 95 at the adjustment gauge 93 lie in each case in a plane, in particular, wherein both planes are parallel to one another and spaced apart from one another. The areas 94, 95 at the adjustment gauge 93 are structured optically with high contrast in order to simplify focusing onto the areas 94, 95.

A second step 102 involves adjusting a first lens 50 of the device 10 such that the first lens 50 generates a—apart from diffraction at the aperture stop of the first lens 50 and imaging aberrations—sharp image of the first area 94 at the adjustment gauge 93 in the light-sensitive layer 32 of a first image sensor 30. The second step 102 is effected in particular by movement of a slide 91, to which the first lens 50 is rigidly connected.

A third step 103 involves adjusting a second lens 60 such that the second lens 60 generates a—apart from diffraction at the aperture stop of the second lens 60 and imaging aberrations—sharp image of the second area 95 at the adjustment gauge 93 in the light-sensitive layer 42 of a second image sensor 40. The third step 103 is performed in particular by movement of the second lens 60 relative to the slide 91.

An optional fourth step 104 involves fixing the second lens 60 relative to the first lens 50, in particular by fixing or rigid mechanical connection of the second lens 60 to the slide 91.

The invention claimed is:

1. A device for capturing a stereoscopic image, comprising:
   a first image sensor including a first light-sensitive layer for capturing a first image;
   a second image sensor including a second light-sensitive layer for capturing a second image;
   a first lens including a first image-side principal plane, said first lens images points lying in a first area sharply onto the first light-sensitive layer of the first image sensor;
   a second lens including a second image-side principal plane, said second lens images points lying in a second area sharply onto the second light-sensitive layer of the second image sensor;
   a slide, at which the first lens is secured rigidly or movably in a direction that is not parallel to an optical axis of the first lens, and at which the second lens is secured rigidly or movably; and
   a slide drive configured to move the slide with the first and second lenses for simultaneously moving the first area and the second area;
   wherein a distance between the first image-side principal plane of the first lens and the first light-sensitive layer of the first image sensor and a distance between the second image-side principal plane of the second lens and the second light-sensitive layer of the second image sensor are different, such that the first area and the second area are spaced apart or offset in a direction parallel to a principal viewing axis of the device.

2. The device according to claim 1, wherein the first lens and the second lens have the same focal length.

3. The device according to claim 1, wherein the light-sensitive layers of the image sensors lie in the same plane; and
   the first image-side principal plane of the first lens and the second image-side principal plane of the second lens are parallel and spaced apart from one another or a line of intersection of the image-side principal planes of the lenses does not intersect the principal viewing axis of the device.

4. The device according to claim 1, wherein the first lens and the second lens have the same focal length, the light-sensitive layers of the image sensors lie in the same plane; and
   the first image-side principal plane of the first lens and the second image-side principal plane of the second lens are parallel and spaced apart from one another or a line of intersection of the image-side principal planes of the lenses does not intersect the principal viewing axis of the device.

5. The device according to claim 1, wherein the light-sensitive layers of the image sensors lie in two different planes which are parallel and spaced apart from one another or a line of intersection of the light-sensitive layers does not intersect the principal viewing axis of the device.

6. The device according to claim 1, wherein the first lens and the second lens have the same focal length, and
   the light-sensitive layers of the image sensors lie in two different planes which are parallel and spaced apart from one another or a line of intersection of the light-sensitive layers does not intersect the principal viewing axis of the device.

7. The device according to claim 1, wherein the first image-side principal plane of the first lens and the second image-side principal plane of the second lens are identical, and
   the image sensors are arranged such that the light-sensitive layers of the image sensors lie in two planes which are parallel and spaced apart from one another.

8. The device according to claim 1, wherein the first lens and the second lens have the same focal length,
   the first image-side principal plane of the first lens and the second image-side principal plane of the second lens are identical, and
   the image sensors are arranged such that the light-sensitive layers of the image sensors lie in two planes which are parallel and spaced apart from one another.

9. A device for capturing a stereoscopic image, including:
   a first image sensor including a first light-sensitive layer for capturing a first image;
   a second image sensor including a second light-sensitive layer for capturing a second image;
   a first lens including a first image-side principal plane, said first lens images points lying in a first area sharply onto the first light-sensitive layer of the first image sensor;
   a second lens including a second image-side principal plane, said second lens images points lying in a second area sharply onto the second light-sensitive layer of the second image sensor;
   a slide, at which the first lens is secured rigidly or movably in a direction that is not parallel to an optical axis of the first lens, and at which the second lens is secured rigidly or movably; and
   a slide drive configured to move the slide for simultaneously moving the first area and the second area;
   wherein the first lens and the second lens are similar to one another,
   wherein a distance between the first lens and the first image sensor is equal to a distance between the second lens and the second image sensor,
   wherein the first lens and the second lens are arranged offset in the direction of a principal viewing axis of the device, such that the first area and the second area are spaced apart or offset in a direction parallel to the principal viewing axis of the device.

10. The device according to claim 9, wherein the first lens and the first image sensor have a first depth of field range,
the second lens and the second image sensor have a second depth of field range, and
the first depth of field range and the second depth of field range overlap.

11. The device according to claim 10, wherein the first area lies within the second depth of field range, and the second area lies within the first depth of field range.

12. The device according to claim 10, wherein the depth of field ranges overlap by at least half of a depth $t_1$ of the first depth of field range and by at least half of a depth $t_2$ of the second depth of field range and by at most two thirds of the depth $t_1$ of the first depth of field range and by at most two thirds of the depth $t_2$ of the second depth of field range.

13. The device according to claim 9, further including:
a lens drive for moving the second lens or a part of the second lens relative to the slide and relative to the first lens and for moving the second area relative to the first area.

14. The device according to claim 9, further including:
a slide, at which the first lens is secured rigidly or movably in a direction that is not parallel to an optical axis of the first lens, and at which the second lens is secured rigidly or movably; and
a slide drive configured to move the slide for simultaneously moving the first area and the second area.

15. The device according to claim 14, further including:
a lens drive for moving the second lens or a part of the second lens relative to the slide and relative to the first lens and for moving the second area relative to the first area.

16. A method for adjusting a device for capturing a stereoscopic image signal during production or maintenance of the device, including the following steps:
arranging an adjustment gauge with a first object and with a second object at a predetermined position relative to the device in such a way that the first object is arranged in a first predetermined plane and the second object is arranged in a second predetermined plane;
adjusting at least one of a first lens and a first image sensor of the device in such a way that the first lens generates a sharp image of the first object at the first image sensor;
adjusting at least one of a second lens and a second image sensor of the device in such a way that the second lens generates a sharp image of the second object at the second image sensor,
wherein the first predetermined plane and the second predetermined plane are in each case orthogonal to a principal viewing axis of the device, wherein the first predetermined plane and the second predetermined plane are parallel to one another and spaced apart from one another.

17. A device for capturing a stereoscopic image, comprising:
a first image sensor including a first light-sensitive layer for capturing a first image;
a second image sensor including a second light-sensitive layer for capturing a second image;
a first lens including a first image-side principal plane, said first lens images points lying in a first area sharply onto the first light-sensitive layer of the first image sensor;
a second lens including a second image-side principal plane, said second lens images points lying in a second area sharply onto the second light-sensitive layer of the second image sensor;
wherein a distance between the first image-side principal plane of the first lens and the first light-sensitive layer of the first image sensor and a distance between the second image-side principal plane of the second lens and the second light-sensitive layer of the second image sensor are different, such that the first area and the second area are spaced apart or offset in a direction parallel to a principal viewing axis of the device;
wherein the light-sensitive layers of the image sensors lie in two different planes which are parallel and spaced apart from one another.

* * * * *